United States Patent [19]
Watanabe et al.

[11] Patent Number: 5,866,731
[45] Date of Patent: Feb. 2, 1999

[54] PROCESS FOR PRODUCING HALOGENATED ORGANIC COMPOUND

[75] Inventors: Kiyoshi Watanabe; Tomoo Matsuura, both of Yokohama, Japan

[73] Assignee: Nippon Zeon Co., Ltd., Tokyo, Japan

[21] Appl. No.: 836,488

[22] PCT Filed: Nov. 9, 1995

[86] PCT No.: PCT/JP95/02292

§ 371 Date: May 5, 1997

§ 102(e) Date: May 5, 1997

[87] PCT Pub. No.: WO96/15084

PCT Pub. Date: May 23, 1996

[30] Foreign Application Priority Data

Nov. 9, 1994 [JP] Japan .................................. 6-300309

[51] Int. Cl.⁶ ............................ C07C 17/08; C07C 17/20
[52] U.S. Cl. ........................ 570/248; 570/249; 570/250
[58] Field of Search .................................. 570/248, 249, 570/250

[56] References Cited

U.S. PATENT DOCUMENTS 5,744,663  4/1998  Landscheidt ............................ 570/250

OTHER PUBLICATIONS

CASREACT #113:190788, abstract of Kropp, J. Am. Chem. Soc., (1990, vol. 112(20), pp. 7433–7434, 1990.

Jikken Kagaku Koza (Lectures on Experimental Chemistry) 20, pp. 193–195, Synthese Organic Compounds [II], (Partial Translation enclosed), 1967.

Shin Jikken Kagaku Koza (Lectures on New Experimental Chemistry) 14, pp. 397–398, Synthesis of Organic Compounds [II] (Partial Translation enclosed), 1958.

J. Org. Chem. 1994, 59 pp. 3102–3112, Surface–Mediated Reactions. 4. Hydrohalogenation of Alkynes, by Paul J. Kropp, et al.

J. Org. Chem. 1980, 45 pp. 3527–2529, Addition of Hydrohalogenic Acids to Alkenes in Aqueous–Organic, Two–Phase Systems in the Presence of Catalytic Amounts of Onium Salts, by Dario Landini, et al.

*Primary Examiner*—D. Margaret M. Mach
*Attorney, Agent, or Firm*—Armstrong, Westerman, Hattori, McLeland & Naughton

[57] ABSTRACT

In a process for producing a halogenated organic compound wherein a hydrogen halide is added to an organic compound having an aliphatic carbon-carbon unsaturated bond, a catalyst is used, which is an organic compound having at least two polar groups in the molecule each containing a heteroatom having an unshared electron pair, and having no aliphatic carbon-carbon unsaturated bond. A typical example of the catalyst is a polyoxyalkylene glycol or a polyol having at least 3 hydroxyl groups.

15 Claims, No Drawings

PROCESS FOR PRODUCING HALOGENATED ORGANIC COMPOUND

This application is a 371 of PCT/JP95/02292, filed 9 Nov. 1995.

TECHNICAL FIELD

This invention relates to a halogenated organic compound which is useful as a raw material for the production of pharmaceuticals, pesticides and functional polymers.

BACKGROUND ART

The processes for preparing a brominated hydrocarbon by adding hydrogen bromide to an alkene compound or an alkyne compound are classified into two types. The first type is a process for introducing a bromine atom to a molecular terminal by a free radical reaction effected by using a free radical initiator such as a peroxide, ultraviolet light, molecular oxygen, a metal such as iron, cobalt or nickel, or α-halo-ketone. The second type is a process for introducing a bromine atom into the inside of a molecule by an ionic reaction effected by using an ionic reaction source such as an ionic phase transfer catalyst, for example, a quaternary ammonium salt, and a Lewis acid (Shin-Jikken Kagaku Koza [New Lecture on Experimental Chemistry], p418; and J. Org. Chem., vol. 45, No. 17, 3527–3529 (1980)) and silica gel (Kagaku to Kogyo (Chem. and Ind.) vol. 45, No. 4, 134 (1992).

The first type process generally has a problem in that a radical source has poor handling properties. The second type process generally has a problem in that an ionic source is troublesome to make and the production is costly.

DISCLOSURE OF INVENTION

An object of the invention is to provide a process for producing a halogenated organic compound by an addition reaction of a hydrogen halide to an organic compound having a carbon-carbon unsaturated bond, wherein a catalyst is used which has a good handling property and is inexpensive and readily available.

In accordance with the present invention, there is provided a process for producing a halogenated organic compound wherein a hydrogen halide is added to an organic compound having an aliphatic carbon-carbon unsaturated bond, as a substrate, characterized by using as a catalyst 0.0001 to 50% by weight, based on the weight of the organic compound having an aliphatic carbon-carbon unsaturated bond, of an organic compound having at least two polar groups in the molecule each containing a heteroatom having an unshared electron pair, and having no aliphatic carbon-carbon unsaturated bond.

PREFERRED EMBODIMENTS FOR CARRYING OUT THE INVENTION

The substrate used in the hydrogen halide addition reaction of the present invention is not particularly limited provided that it is an organic compound having at least one aliphatic carbon-carbon unsaturated bond in the molecule. As the substrate, there can be mentioned generally alkenes and alkynes. The alkenes and alkynes are represented by the following formulae (1) and (2), respectively:

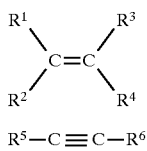

In the above formulae, $R^1$, $R^2$, $R^3$, $R^4$, $R^5$ and $R^6$ may be the same or different, and are selected from a hydrogen atom, an alkyl group, an alkoxy group, an aryl group, an aralkyl group, a phenoxy group, a halogen atom, a hydroxyl group, a carboxyl group and a nitro group, and $R^1$ and $R^3$ in formula (1) may form a ring and $R^5$ and $R^6$ in formula (2) may form a ring, together with the carbon atoms of the carbon-carbon unsaturated bond.

The number of carbon atoms in each of the alkyl, alkoxy, aryl, aralkyl and phenoxy groups is not particularly limited, but is usually in the range of 1 to 20, preferably 1 to 15 and more preferably 1 to 10. In the case where $R^1$ and $R^3$ in formula (1) form a ring and $R^5$ and $R^6$ in formula (2) form a ring, together with the carbon atoms of the carbon-carbon unsaturated bond, each of the rings is usually a 4-membered to 20-membered ring, preferably 4-membered to 10-membered ring and more preferably 5-membered or 6-membered ring.

The alkyl, alkoxy, aryl, aralkyl and phenoxy groups may have a substituent or substituents. The substituents are not particularly limited unless the substituents have baneful effects on the halogenation reaction.

The number of carbon atoms in each of the alkenes and alkynes is not particularly limited and is usually in the range of 2 to 30, preferably 3 to 20 and more preferably 5 to 10.

As specific examples of the alkenes represented by formula (1), there can be mentioned 1-butene, 2-butene, 1-octene, 2-heptadecene, cyclobutene, cyclopentene, cyclohexene, cyclooctene, styrene, α-methylstyrene, 1,2-diphenylethylene, 4-bromo-2-butene, 1-bromo-1-octene, 4-vinyl-1-cyclohexene, 1-acetoxy-3-butene, 3-hexenol, 10-undecen-1-ol, 10-undecenoic acid and 1-nitro-1-propene of these, 1-octene, cyclopentene, cyclohexene, cyclooctene and styrene are preferable.

As specific examples of the alkynes represented by formula (2), there can be mentioned 1-hexyne, cyclohexylacetylene, 2-nonyne, 1-heptyne, phenylacetylene, 1,2-diphenylacetylene, 3-bromophenylacetylene, propargyl alcohol, 3-hexynol, 1-phenoxy-3-hexyne, 3-nitrophenylacetylene and 1-ethoxy-2-hexyne. Of these, 1-heptyne, phenylacetylene and 3-hexynol are preferable.

As specific examples of the hydrogen halide, there can be mentioned hydrogen bromide, hydrogen chloride, hydrogen iodide and hydrogen fluoride of these, hydrogen bromide and hydrogen chloride are preferable. Hydrogen bromide is especially preferable. The amount of the hydrogen fluoride is usually at least 0.9 mole, preferably 1 to 10 moles and more preferably 1 to 5 moles, per mole of the substrate.

As typical examples of the hydrogenated hydrocarbons produced by the hydrogen halide addition reaction of the above-mentioned alkenes and alkynes, there can be mentioned adducts to alkenes such as 1-bromoheptane, cyclopentyl bromide, cyclopentyl fluoride, cyclopentyl iodide, cyclohexyl bromide, 1-bromo-1-phenylethane, 1-chloro-1-phenylethane, 10-bromoundecanoic acid and 7-bromotetradecanoic acid; and adducts to alkynes such as 1-bromo-2-phenylethylene and 1-bromo-1-heptene and 3-bromo-1- hexenol. Especially the process of the present invention is useful for the production of a terminal-halogenated hydrocarbon from an alkene or alkyne having a terminal carbon-carbon unsaturated bond, and of a halogenated cyclic hydrocarbon from a cyclic alkene or a cyclic alkyne.

The catalyst used in the present invention is an organic compound which has at least two polar groups in the molecule each containing a heteroatom having an unshared electron pair, and does not have an aliphatic carbon-carbon unsaturated bond. Usually the catalyst is an aromatic or aliphatic hydrocarbon having such polar groups. As the heteroatom contained in the polar groups, there can be mentioned heteroatoms belonging to group 5B to 6B in the second to fourth period in the periodic table. The typical examples thereof include nitrogen, oxygen, sulfur and phosphorus. Of these, nitrogen and oxygen are preferable. Oxygen is most preferable.

As specific examples of the polar groups having such heteroatoms, there can be mentioned a hydroxyl group, an oxy group, a carbonyl group, a carboxyl group, a sulfonyl group, a thiocarbonyl group, an amino group, an amide group and a hydrazo group. Of these, a hydroxyl group, an oxy group and an amino group are preferable. A hydroxyl group and an oxy group are especially preferable.

As typical examples of the catalyst, those which are represented by the following formula (3) are mentioned.

$$R^7\text{-}(A\text{-}X)_m\text{-}R^8 \quad (3)$$

The catalysts represented by formula (3) include chain and cyclic alkylene glycols and derivatives thereof, polyoxyalkylene glycols and derivatives, and polyamines and derivatives thereof.

In formula (3), A is an alkylene group which may be branched and which has usually 1 to 10 carbon atoms, preferably 2 to 5 carbon atoms more preferably 2 carbon atoms. X is an oxy group or a group represented by the formula —NR$^9$— where R$^9$ is a hydrogen atom or a lower alkyl group. R$^7$ represents a hydroxyl group, an alkoxy group, a phenoxy group, an acyloxy group, an amino group, an alkylamino group, a dialkylamino group or an acylamino group. R$^8$ represents a hydrogen atom, an alkyl group, an aryl group or an acyl group. R$^7$ and R$^8$ may form a ring together with the group -(A—X)$_m$-. m is an integer of 2 to 500, preferably 2 to 300. The number of carbon atoms in each of these alkoxy group, phenoxy group, acyloxy group, alkylamino group, dialkylamino group and acylamino group is usually 1 to 20, preferably 1 to 15 and more preferably 1 to 10. The number of carbon atoms in each of the alkyl, aryl and acyl groups is usually 1 to 20, preferably 1 to 15 and more preferably 1 to 10.

As specific examples of the compound represented by formula (3), there can be mentioned alkylene glycols such as ethylene glycol, propylene glycol, 2-methyl-1,3-propanediol, tetramethylene glycol, neopentyl glycol and hexamethylene glycol; ether derivatives of alkylene glycols such as ethylene glycol monomethyl ether, ethylene glycol monoethyl ether, propylene glycol monomethyl ether, ethylene glycol dimethyl ether and ethylene glycol diethyl ether; chain oligo-oxyalkylene glycols and polyoxyalkylene glycols such as diethylene glycol, dipropylene glycol, triethylene glycol, tripropylene glycol, tetraethylene glycol, penta-ethylene glycol, polyethylene glycol, polypropylene glycol and polyoxyethylene-polyoxypropylene block copolymer; ether derivatives of chain oligo-oxyalkylene glycols such as diethylene glycol monomethyl ether, diethylene glycol monohexyl ether, dipropylene glycol monomethyl ether, diethylene glycol dimethyl ether, diethylene glycol dibutyl ether, triethylene glycol monoisopropyl ether, triethylene glycol mono-n-butyl ether, triethylene glycol monododecyl ether, tripropylene glycol monomethyl ether, triethylene glycol dimethyl ether, tetraethylene glycol monododecyl ether and tetraethylene glycol dimethyl ether; ether-ester derivatives of chain oligo-oxyalkylene glycols such as diethylene glycol monomethyl ether monoacetate; ester derivatives of chain oligo-oxyalkylene glycols such as diethylene glycol diacetate; ether derivatives of chain polyoxyalkylene glycols such as polyoxyethylene alkyl ether, polyoxyethylene alkylphenyl ether and polyoxyethylene-polyoxypropylene alkyl ether, ester derivatives of chain polyoxyalkylene glycols such as polyethylene glycol fatty acid ester and polypropylene glycol fatty acid ester; nitrogen-containing derivatives of chain polyoxyalkylene glycols, such as polyoxyethylene fatty acid amide and polyoxyethylene alkylamine; chain polyamines such as putrescine, spermine, spermidine and polyethylene imine; cyclic ethers such as dioxane, 18-crown-6-ether, 15-crown-5-ether, 12-crown-4-ether, dibenzo-18-crown-6-ether, dibenzo-24-crown-8-ether and dicyclohexano-18-crown-6-ether and 4'-nitrobenzo-15-crown-5-ether; and cyclic polyamines such as 1,4,7,10-tetraazacyclododecane; cyclic amino ethers such as 1-aza-15-crown-5-ether. Of these compounds, alkylene glycols and derivatives thereof, chain oligo-oxyalkylene glycols and derivatives thereof, chain polyoxyalkylene glycols and derivatives thereof, cyclic ethers and cyclic amines are preferable. Alkylene glycols and derivatives, chain polyoxyalkylene glycols and derivatives, and cyclic ethers are especially preferable.

Other typical examples of the catalyst used in the process of the present invention include polyols and derivatives, having at least three hydroxyl groups. As specific examples of the polyol, there can be mentioned polyvinyl alcohol and vinyl acetate polymers such as modified ethylene-vinyl acetate copolymer and modified ethylene-vinyl acetate-acrylic acid copolymer; saccharides including monosaccharides such as glycerol, mannitol, threitol, arabitol, xylitol, glucose and fructose, disaccharides such as trehalose, sucrose, maltose and lactose, oligosaccharide such as oligoglucose, cyclic polysaccharides such as α-, β-, and γ-cyclodextrins, and chain saccharides such as mannitol, sorbitol, mannose, glucronic acid, dextrin, pluran, cellulose and chitin; polyphenols such as 5,11,17,23,29,35-hexa-t-butyl-37,38,39,41,42-hexahydroxycalix[6]arene; and pentaerithritol, phenoxy resin and ketone resin. Of these polyols, saccharides are preferable, and cyclic polysaccharides are especially preferable.

As specific examples of the polyol derivatives, there can be mentioned polyvinyl ether derivatives such as polyvinyl methyl ether and polyvinyl isobutyl ether; acetals of polyvinyl alcohol such as polyvinyl formal; polyglycerine fatty acid ester; and ethers, esters and amides of the above-listed saccharides.

The above-mentioned compounds used as the catalyst have a molecular weight of usually in the range of 40 to 50,000, preferably 50 to 20,000 and more preferably 60 to 10,000. The molecular weight of a low molecular weight is calculated from its chemical formula. The molecular weight of polyethylene glycol is calculated from the content of hydroxyl groups perunit weight thereof. The molecular weight of polyvinyl alcohol is determined by gel permeation chromatography.

The above-mentioned compounds used as the catalyst may be used either alone or in combination. The amount of the catalyst used is usually in the range of 0.0001 to 50% by weight, preferably 0.001 to 20% by weight and more preferably 0.005 to 10% by weight, based on the weight of the substrate.

The addition reaction of hydrogen halide to the substrate having an aliphatic carbon-carbon unsaturated bond is conducted at a temperature not higher than the boiling point of the solvent, usually in the range of −80° to 200° C., preferably −50° to 150° C. and more preferably −20° to 100° C., usually under atmospheric pressure for not longer than 24 hours, preferably 30 minutes to 15 hours and more preferably 1 to 10 hours.

As the solvent used as the reaction medium, those which do not react with a hydrogen halide are used. The reaction can be conducted without the use of a solvent. As the specific examples of the solvent, there can be mentioned aromatic hydrocarbons such as benzene, toluene and xylene, alicyclic hydrocarbons such as cyclohexane and cyclopentane, aliphatic hydrocarbons such as pentane and hexane, and halogenated hydrocarbons such as chloroform, methylene chloride and trichloroethane, and carbon tetrachloride, After completion of the reaction, conventional treatments such as liquid separation, extraction, washing, drying and concentration are carried out to give the corresponding halogenated organic compound.

EXAMPLE 1

A reactor was charged with 100 milli-moles of an unsaturated hydrocarbon shown in Table 1, 30 milli-liters of dichloromethane and 1% by weight, based on the weight of the unsaturated hydrocarbon, of polyethylene glycol (molecular weight of 4,000; hereinafter abbreviated to "PEG-4000"). At a temperature of 0° C. and under atmospheric pressure, 150 milli-moles of hydrogen bromide gas was introduced in the flask over a period of 4 hours to conduct a reaction. After completion of the reaction, the reaction product was extracted with dichloromethane. The thus-obtained organic phase was washed with an aqueous saturated sodium hydrogen-carbonate solution and then distilled under a reduced pressure to give the intended compound. The results are shown in Table 1.

TABLE 1

| Run | Unsaturated hydrocarbon | Produced halogenated hydrocarbon | Boiling point (°C. at given reduced pressure) | Yield (%) |
|---|---|---|---|---|
| 1-1 | 1-Heptene | 1-Bromo-heptane | 70–75 (18 mmHg) | 80.5 |
| 1-2 | 1-Heptyne | 1-Bromo-1-heptene | 64–74 (20 mmHg) | 80.8 |
| 1-3 | Styrene | 1-Bromo-1-phenylethane | 101–105 (26 mmHg) | 86.8 |
| 1-4 | Cyclopentene | Cyclopentyl bromide | 64–66 (64 mmHg) | 80.1 |
| 1-5 | Cyclohexene | Cyclohexyl bromide | 57–58 (18 mmHg) | 80.0 |

As seen from Table 1, when an alkene or alkyne having a terminal unsaturated bond is used as the starting material, the corresponding terminally halogenated hydrocarbon is produced in a good yield (Run 1-1 and Run 1-2). However, when a conjugated olefin is used as the starting material, a mid part of the olefin is halogenated (Run 1-3). When a cycloalkene is used as the starting material, a halogenated cyclohydrocarbon is obtained in a good yield (Run 1-4 and Run 1-5).

EXAMPLE 2

The procedures employed in Example 1 were repeated to produce cyclopentyl bromide wherein 100 milli-moles of a cyclopentene, 150 milli-moles of hydrogen bromide gas, a catalyst shown in Table 2 (in an amount of 2% by weight based on the weight of the substrate) and a solvent were used with all other conditions remaining the same.

TABLE 2

| Run | Catalyst | Solvent | Yield (%) |
|---|---|---|---|
| 2-1 | PEG-4000 | Dichloromethane | 80.1 |
| 2-2 | PEG-4000 | Cyclopentane | 77.3 |
| 2-3 *1 | Polyethylene glycol dimethyl ether | Dichloromethane | 60.4 |
| 2-4 | β-Cyclodextrin | Dichloromethane | 76.6 |
| 2-5 | Polyvinyl alcohol *2 | Dichloromethane | 51.6 |
| 2-6 | Pentaerythritol | Dichloromethane | 54.2*3 |
| C.EX. *4 | | Dichloromethane | 40.0*3 |

*1 Molecular weight = 1,000
*2 Molecular weight = 2,000, saponification degree = 80% by mole
*3 Conversion (%)
*4 Control example wherein a catalyst is not used.

As seen from Table 2, polyethylene glycol and derivatives thereof exhibit a high catalyst activity (Run 2-1, 2-2 and 2-3). Among polyols (Run 2-4, 2-5 and 2-6), β-cyclodextrin exhibits especially high activity (Run 2-4).

EXAMPLE 3

To 136.9 g (1.35 moles) of an aqueous hydrogen chloride solution of a 36% concentration, 1.0 g (5% by weight based on the weight of cyclopentene) of polyethylene glycol 200 (molecular weight of 200, hereinafter abbreviated to "PEG-200") was added. Then 20.4 g (0.3 mole) of cycloperitene was added at a temperature not higher than 20° C. and heated under reflux for 6 hours to conduct a reaction.

After completion of the reaction, the reaction product was extracted with dichloromethane. The thus-obtained organic phase was washed with an aqueous saturated sodium carbonate solution. Dichloromethane was recovered at atmospheric pressure, and the liquid was distilled under a reduced pressure to give 20.7 g of colorless transparent liquid (cyclopentyl chloride) having a boiling point of 73° C. (280 milli-bar) (yield: 65.9%).

EXAMPLE 4

Cyclopentyl chloride was produced by the same procedures as employed in Example 3 except that 5% by weight, based on the weight of cyclopentene, of β-cyclodextrin was used instead of PEG-200. The yield was 55%.

EXAMPLE 5

Cyclopentyl bromide was produced by the same procedures as employed in Example 1 except that 500 milli-moles of a cyclopentene, 750 milli-moles of hydrogen bromide and a catalyst shown in Table 3 (the amount of the catalyst also is shown in Table 3) were used. The results are shown in Table 3.

TABLE 3

| Run | Catalyst | Amount *1 (wt %) | Yield (%) |
|---|---|---|---|
| 5-1 | PEG-200 | 1 | 80.8 |
| 5-2 | PEG-4000 | 0.015 | 81.9 |
| 5-3 | PEG-4000 | 0.1 | 88.7 |
| 5-4 | 18-Crwon-6 *2 | 1 | 88.0 |
| 5-5 | 12-Azacrown-4 *3 | 1 | 80.0 |
| 5-6 | Dioxane | 1 | 82.0 |
| 5-7 | Calix-Allen *4 | 1 | 77.0 |
| 5-8 | Glycerine | 1 | 66.0 |
| 5-9 | Ethylene glycol | 0.1 | 70.4 |
| 5-10 | EGDM *5 | 0.1 | 81.6 |
| 5-12 | EGDM *5 | 1 | 83.0 |
| C.EX.1 | EGDM *5 | 150 | 62.0*6 |

*1 % by weight based on the weight of the substrate
*2 1,4,7,10,13,16-Hexaoxacyclooctadecane
*3 1,4,7,10-Tetraazacyclododecane
*4 5,11,17,23,29,35-Hexa-t-butyl-37,38,39,40,41,42-hexahydroxycalix[6]arene
*5 Ethylene glycol dimethyl ether
*6 Conversion As seen from Table 3, even though the amount of the catalyst is only 0.015% by weight based on the weight of the substrate, the catalyst exhibited a high activity (Run 5-2). In contrast, when the amount of the catalyst is too large, the catalyst activity is drastically reduced (Comparative Example 1). Polyols such as polyphenols, e.g., calixarene, and glycerine exhibit a high catalyst activity (Run 5-7 and 5-8). Cyclic compounds having a heteroatom such as cyclic ethers (Run 5-4 and 5-6) and a cyclic polyamine (Run 5-5) exhibit a high catalyst activity. Especially cyclic ethers exhibits good catalyst activity.

Industrial Applicability

The catalyst used for the hydrogen halide addition reaction in the process of the present invention exhibits high catalyst activity, has good handling property and is generally inexpensive and readily available. Thus the process of the present invention is industrially advantageous as a process for halogenating an organic compound having an aliphatic carbon-carbon unsaturated bond.

We claim:

1. A process for producing a halogenated organic compound comprising: adding a hydrogen halide to an organic compound having an aliphatic carbon-carbon unsaturated bond, as a substrate, using 0.0001 to 50% by weight, based on the weight of the organic compound having an aliphatic carbon-carbon unsaturated bond, of a catalyst, said catalyst having at least two polar groups in the molecule each containing a heteroatom having an unshared electron pair, and having no aliphatic carbon-carbon unsaturated bond, said catalyst being a compound represented by the following formula:

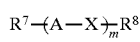

wherein A is an alkylene group which may be branched, X is an oxy group or a group represented by the formula:

where $R^9$ is a hydrogen atom or a lower alkyl group, $R^7$ represents a hydroxyl group, an alkoxy group, a phenoxy group, an acyloxy group, an amino group, an alkylamino group, a dialkylamino group or an acylamino group, $R^8$ represents a hydrogen atom, an alkyl group, an aryl group or an acyl group, $R^7$ and $R^8$ may form a ring together with the group $(A-X)_m$, and m is an integer 2 to 500.

2. A process for producing a halogenated organic compound comprising: adding a hydrogen halide to an organic compound having an aliphatic carbon-carbon unsaturated bond, as a substrate, using 0.0001 to 50% by weight, based on the weight of the organic compound having an aliphatic carbon-carbon unsaturated bond, of a catalyst having at least two polar groups in the molecule each containing a heteroatom having an unshared electron pair, and having no aliphatic carbon-carbon unsaturated bond, said catalyst being selected from polyols and derivatives thereof, which have at least 3 hydroxyl groups.

3. The process for producing the halogenated organic compound according to claim 2, wherein the polyol is selected from polyvinyl alcohol, vinyl acetate polymers, saccharides and polyphenols.

4. The process for producing the halogenated organic compound according to claim 1, wherein the substrate is an alkene or an alkyne.

5. The process for producing the halogenated organic compound according to claim 4, wherein the alkene and the alkyne are represented by the following formulae, respectively:

wherein $R^1$, $R^2$, $R^3$, $R^4$, $R^5$ and $R^6$ may be the same or different, and are selected from a hydrogen atom, an alkyl group, an alkoxy group, an aryl group, an aralkyl group, a phenoxy group, a halogen atom, a hydroxyl group, a carboxyl group and a nitro group, and $R^1$ and $R^3$ in formula (1) may form a ring and $R^5$ and $R^6$ in formula (2) may form a ring, together with the carbon atoms of the respective carbon-carbon unsaturated bond.

6. The process for producing the halogenated organic compound according to claim 1, wherein the substrate has 2 to 20 carbon atoms.

7. The process for producing the halogenated organic compound according to claim 1, wherein the hydrogen halide is hydrogen bromide or hydrogen chloride.

8. The process for producing the halogenated organic compound according to claim 1, wherein the amount of the hydrogen halide is at least 0.9 mole per mole of the substrate.

9. The process for producing the halogenated organic compound according to claim 2, wherein the substrate is an alkene or an alkyne.

10. The process for producing the halogenated organic compound according to claim 9, wherein the alkene and the alkyne are represented by the following formulae, respectively:

wherein $R^1$, $R^2$, $R^3$, $R^4$, $R^5$ and $R^6$ may be the same or different, and are selected from a hydrogen atom, an alkyl group, an alkoxy group, an aryl group, an aralkyl group, a phenoxy group, a halogen atom, a hydroxyl group, a carboxyl group and a nitro group, and $R^1$ and $R^3$ in formula (1) may form a ring and $R^5$ and $R^6$ in formula (2) may form a ring, together with the carbon atoms of the respective carbon-carbon unsaturated bond.

11. The process for producing the halogenated organic compound according to claim 2, wherein the substrate has 2 to 20 carbon atoms.

12. The process for producing the halogenated organic compound according to claim 2, wherein the hydrogen halide is hydrogen bromide or hydrogen chloride.

13. The process for producing the halogenated organic compound according to claim 2, wherein the amount of the hydrogen halide is at least 0.9 mole per mole of the substrate.

14. The process for producing the halogenated organic compound according to claim 2, wherein the catalyst has a molecular weight of 40 to 50,000.

15. The process for producing the halogenated organic compound according to claim 1, wherein the catalyst has a molecular weight of 40 to 50,000.

* * * * *